US00PP28384P2

(12) United States Plant Patent
Geibel

(10) Patent No.: US PP28,384 P2
(45) Date of Patent: Sep. 12, 2017

(54) ***PELARGONIUM* PLANT NAMED 'PACTIORED'**

(50) Latin Name: *Pelargonium×hortorum×Pelargonium peltatum*
Varietal Denomination: PACTIORED

(71) Applicant: Martin Geibel, Dresden (DE)

(72) Inventor: Martin Geibel, Dresden (DE)

(73) Assignee: Elsner pac Jungplanzen GbR, Dresden (DE)

( * ) Notice: Subject to any disclaimer, the term of this patent is extended or adjusted under 35 U.S.C. 154(b) by 0 days.

(21) Appl. No.: 14/999,454

(22) Filed: May 9, 2016

(51) Int. Cl.
*A01H 5/02* (2006.01)

(52) U.S. Cl.
USPC ..... Plt./324

(58) Field of Classification Search
USPC ..... Plt./324
See application file for complete search history.

*Primary Examiner* — Annette Para
(74) *Attorney, Agent, or Firm* — C. A. Whealy

(57) ABSTRACT

A new and distinct Interspecific Geranium plant named 'Pactiored', characterized by its upright and uniformly mounding plant habit; vigorous growth habit and rapid growth rate; freely basal branching habit; dark green-colored leaves with a distinct zonation pattern; early and freely flowering habit; dark red-colored single-type flowers held above the foliar plane on strong peduncles; and good garden performance.

1 Drawing Sheet

Botanical designation: *Pelargonium×hortorum×Pelargonium peltatum.*

Cultivar denomination: 'PACTIORED'.

BACKGROUND OF THE INVENTION

The present invention relates to a new and distinct cultivar of Interspecific Geranium plant, botanically known as *Pelargonium×hortorum×Pelargonium peltatum*, and hereinafter referred to by the cultivar name 'Pactiored'.

The new Interspecific Geranium plant is a product of a planned breeding program conducted by the Inventor in Dresden, Germany. The objective of the breeding program is to develop new vigorous Interspecific Geranium plants with numerous attractive flowers and good garden, performance.

The new Interspecific Geranium plant originated from a cross-pollination made by the Inventor in Dresden, Germany during the summer of 2010 of two unnamed proprietary selections of *Pelargonium×hortorum*, not patented. The new Interspecific Geranium plant was discovered and selected by the Inventor as a flowering plant from within the progeny of the stated cross-pollination in a controlled greenhouse environment in Dresden, Germany in June, 2011.

Asexual reproduction of the new Interspecific Geranium plant by vegetative terminal cuttings in a controlled greenhouse environment in Dresden, Germany since January, 2012 has shown that the unique features of this new Interspecific Geranium plant are stable and reproduced true to type in successive generations.

SUMMARY OF THE INVENTION

Plants of the new Interspecific Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pactiored'. These characteristics in combination distinguish 'Pactiored' as a new and distinct Interspecific Geranium plant:

1. Upright and uniformly mounding plant habit.
2. Vigorous growth habit and rapid growth rate.
3. Freely basal branching habit.
4. Dark green-colored leaves with a distinct zonation pattern.
5. Early and freely flowering habit.
6. Dark red-colored single-type flowers held above the foliar plane on strong peduncles.
7. Good garden performance.

Plants of the new Interspecific Geranium differ primarily from plants of the parent selections in plant habit as plants of the new Interspecific Geranium are more uniform than plants of the parent selections.

Plants of the new Interspecific Geranium can be compared to plants of the *Pelargonium×hortorum×Pelargonium tongaenense* 'Carte Dereds', disclosed in U.S. Plant Pat. No. 15,616. In side-by-side comparisons, plants of the new Interspecific Geranium differ from plants of 'Cante Dereds' in the following characteristics:

1. Plants of the new Interspecific Geranium are smaller than plants of 'Cante Dereds'.
2. Plants of the new Interspecific Geranium have shorter internodes than plants of 'Cante Dereds'.
3. Plants of the new Interspecific Geranium are more densely foliated than plants of 'Cante Dereds'.
4. Leaves of plants of the new Interspecific Geranium have a more distinct zonation pattern than leaves of plants of 'Cante Dereds'.
5. Plants of the new Interspecific Geranium have smaller petals than plants of 'Cante Dereds'.
6. Plants of the new Interspecific Geranium are more high temperature tolerant than plants of 'Cante Dereds'.

Plants of the new Interspecific Geranium can also be compared to plants of the *Pelargonium×hortorum×Pelargonium peltatum* 'Pactioscar', disclosed in U.S. Plant patent application Ser. No. 14/545,189. In side-by-side comparisons, plants of the new Interspecific Geranium differ from plants of 'Pactioscar' in the following characteristics:

1. Plants of the new Interspecific Geranium are shorter and more upright than plants of 'Pactioscar'.
2. Plants of the new Interspecific Geranium had single-type flowers whereas plants of 'Pactioscar' had semi-double flowers.
3. Plants of the new Interspecific Geranium have smaller petals than plants of 'Pactioscar'.
4. Plants of the new Interspecific Geranium and 'Pactioscar' differ in flower color as plants of 'Pactioscar' have bright scarlet-colored flowers.
5. Plants of the new Interspecific Geranium have shorter peduncles and pedicels than plants of 'Pactioscar'.
6. Flowers of plants of the new Interspecific Geranium produce less pollen than flowers of plants of 'Pactioscar'.

BRIEF DESCRIPTION OF THE PHOTOGRAPH

The accompanying colored photograph illustrates the overall appearance of the new Interspecific Geranium plant showing the colors as true as it is reasonably possible to obtain in colored reproductions of this type. Colors in the photograph may differ slightly from the color values cited in the detailed botanical description which accurately describe the colors of the new Interspecific Geranium plant.

The photograph comprises a side perspective view of a typical flowering plant of 'Pactiored' grown in a container.

DETAILED BOTANICAL DESCRIPTION

The aforementioned photograph and following observations, measurements and values describe plants grown in 19-cm containers during the summer in a glass-covered greenhouse in Dresden, Germany and under cultural practices typical of commercial Interspecific Geranium production. During the production of the plants, day temperatures averaged 18° C., night temperatures averaged 16° C. and light levels ranged from 15 kilolux to 100 kilolux. Plants were nine months old when photograph and the detailed description were taken. In the detailed description, color references are made to The Royal Horticultural Society Colour Chart, 1995 Edition, except where general terms of ordinary dictionary significance are used.

Botanical classification: *Pelargonium×hortorum×Pelargonium peltatum* 'Pactiored'.

Parentage:

*Female, or seed, parent*.—Unnamed proprietary selection of *Pelargonium×hortorum*, not patented.

*Male or pollen parent*.—Unnamed proprietary selection of *Pelargonium peltatum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer*.—About four weeks at temperatures about 20° C.

*Time to produce a rooted young plant, winter*.—About four weeks at temperatures about 18° C.

*Root description*.—Fine, fibrous; white in color.

*Rooting habit*.—Freely branching; dense.

Plant description:

*Plant and growth habit*.—Upright and uniformly mounding plant habit; inverted triangle; densely foliated; vigorous growth habit; rapid growth rate; freely basal branching habit with numerous lateral branches developing per plant; pinching is not required.

*Plant height, to top of umbels*.—About 29 cm.

*Plant height, to top of foliar plane*.—About 23 cm.

*Plant width*.—About 60 cm.

*Lateral branches*.—Length: About 22 cm. Diameter: About 5 mm. Internode length: About 1.5 cm. Texture: Pubescent. Color: Close to 146C.

Leaf description:

*Arrangement*.—Mostly opposite; simple.

*Length*.—About 3.5 cm.

*Width*.—About 6 cm.

*Shape*.—Rounded; roughly reniform.

*Apex*.—Rounded.

*Base*.—Cordate, open.

*Margin*.—Crenate.

*Venation pattern*.—Palmate.

*Texture, upper and lower surfaces*.—Pubescent; felt-like.

*Color*.—Developing and fully expanded leaves, upper surface: Close to 137B; venation, close to 137B. Developing and fully expanded leaves, lower surface: Close to 147B; venation, close to 146C. Zonation pattern: Intensity: Strong. Location: About 1 cm from margin. Width: About 1 cm. Color: Close to darker than 147A.

*Petioles*.—Length: About 3.5 cm. Diameter: About 2 mm. Texture, upper and lower surfaces: Pubescent; rough. Color, upper and lower surfaces: Close to 147B.

Flower description:

*Flower arrangement and flowering habit*.—Single-type flowers arranged in hemispherical umbels arising from apical leaf axils; umbels displayed above the foliar plane on strong peduncles; flowers face upright to outwardly; freely flowering habit with about ten flowers per umbel with numerous umbels developing per plant.

*Fragrance*.—None detected.

*Flowering season*.—Early flowering habit, plants begin flowering about 70 days after planting; in the garden in Germany, flowering begins in April and continues until frost in the autumn.

*Flower longevity*.—Flowers last about six to ten days on the plant; umbels last about three to four weeks on the plant; flowers not persistent.

*Umbel height*.—About 3.5 cm.

*Umbel diameter*.—About 7 cm.

*Flower diameter*.—About 3.2 cm.

*Flower depth (height)*.—About 2 cm.

*Flower buds*.—Length: About 1 cm. Diameter: About 5 mm. Shape: Spindle-shaped. Color: Close to 144A.

*Petals*.—Quantity per flower: About five arranged in a single whorl; petals somewhat imbricate. Length: About 2.1 cm to 2.2 cm. Width: About 1.3 cm. Shape: Obovate. Apex: Rounded. Base: Cuneate. Margin: Entire. Texture, upper and lower surfaces: Smooth, glabrous; velvety. Color: When opening and fully opened, upper surface: Close to darker than 45A; towards the base, close to 155D; venation, close to 187A; color does not change with development. When opening and fully opened, lower surface: Close to 46B; towards the base, close to 155D; venation, close to 46B.

*Petaloids*.—None observed on plants of the new Interspecific Geranium plant.

*Sepals*.—Quantity per flower: Five arranged in a single whorl. Length: About 1 cm. Width: About 3 mm. Shape: Lanceolate. Apex: Acute. Margin: Entire. Texture, upper and lower surfaces: Pubescent. Color, upper and lower surfaces: Close to 144A.

*Peduncles* (*umbel stems*).—Length: About 11 cm. Diameter: About 3 mm. Strength: Strong. Angle: Mostly upright. Texture: Pubescent. Color: Close to 144A.

*Pedicels* (*individual flower stems*).—Length: About 1.4 cm. Diameter: About 1 mm. Strength: Moderately strong; flexible. Texture: Pubescent. Color: Close to 144A.

*Reproductive organs*.—Androecium: Stamen quantity per flower: About nine. Anther length: About 2 mm. Anther shape: Tubular. Anther color: Close to 165A. Pollen amount: Scarce. Pollen color: Close to 167A. Gynoecium: Pistil quantity per flower: One. Pistil length: About 9 mm. Stigma shape: Five-parted. Stigma color: Close to 58A. Style length: About 2 mm. Style color: Close to 196D Ovary color: Close to 139D. Seeds and fruits: Seed and fruit development have not been observed on plants of the new Interspecific Geranium.

Disease & pest resistance: Plants of the new Interspecific Geranium have not been observed to be resistant to pathogens and pests common to Interspecific Geraniums.

Garden performance: Plants of the new Interspecific Geranium have been observed to have good garden performance and to tolerate temperatures ranging from about 1° C. to about 35° C. to 40° C.

It is claimed:

1. A new and distinct Interspecific Geranium plant named 'Pactiored' as illustrated and described.

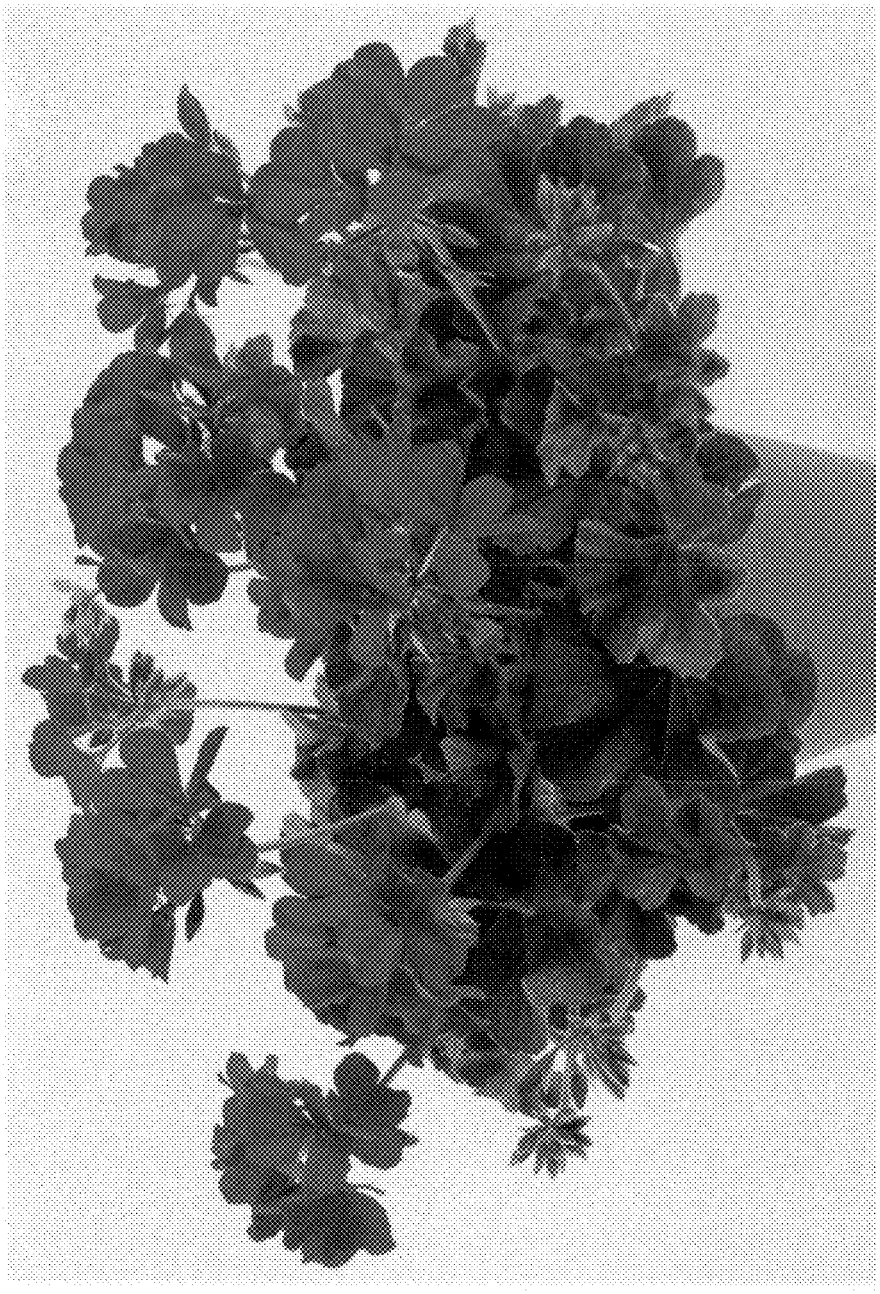

* * * * *